United States Patent [19] [11] 4,113,865
Dondi et al. [45] Sep. 12, 1978

[54] FRUIT JUICE-SUGAR GRANULES

[75] Inventors: Gilberto Dondi; Arnaldo Zanotti, both of Milan, Italy

[73] Assignee: Bayer Italia Societa per Azioni, Italy

[21] Appl. No.: 743,853

[22] Filed: Nov. 22, 1976

[30] Foreign Application Priority Data

Nov. 28, 1975 [IT] Italy ................................ 29799 A/75

[51] Int. Cl.² ...................... A61K 9/46; A61K 31/375; A61K 31/61
[52] U.S. Cl. ...................................... 424/230; 424/44; 424/234; 424/280; 424/361; 426/72; 426/330.5; 426/569; 426/590; 426/591; 426/599
[58] Field of Search ............... 426/72, 330.5, 569, 426/590, 591, 599; 424/44, 230, 234, 280, 361

[56] References Cited

U.S. PATENT DOCUMENTS

| 1,361,079 | 12/1920 | McDill | 426/599 |
|---|---|---|---|
| 1,556,572 | 10/1925 | Pierce | 426/599 X |
| 1,594,804 | 8/1926 | Welch | 426/599 |
| 1,619,202 | 3/1927 | Greenstreet | 426/599 |
| 1,810,276 | 6/1931 | Jameson et al. | 426/599 |
| 1,915,911 | 6/1933 | Allen | 426/599 |
| 2,471,678 | 5/1949 | Flosdorf | 426/599 X |
| 2,567,038 | 9/1951 | Stevens et al. | 426/599 X |
| 2,834,687 | 5/1958 | Swisher | 426/599 |
| 3,773,922 | 11/1973 | Gergely | 424/44 |
| 3,953,615 | 4/1976 | Gupta et al. | 426/599 X |

FOREIGN PATENT DOCUMENTS

| 1,299,994 | 7/1969 | Fed. Rep. of Germany. | |
| 1,188,871 | 4/1970 | United Kingdom | 426/599 |

Primary Examiner—Shep K. Rose
Attorney, Agent, or Firm—Jacobs & Jacobs

[57] ABSTRACT

Granules of a maximum grain size of 1 mm comprising from 8 to 12% fruit juice solids with the balance being predominantly sugar and no more than 0.05% water are prepared. The granules are particularly useful as flavoring agents in the formulation of pharmaceutical compositions of hydrolytically unstable agents.

10 Claims, No Drawings

FRUIT JUICE-SUGAR GRANULES

DETAILED DESCRIPTION

The present invention pertains to a process for the preparation of substantially anhydrous fruit juice granules and which can be used as flavor improving agents. They are particularly useful in combination with pharmaceutical agents which are sensitive to hydrolysis such as acetylsalicylic acid.

It is known that citrus oil can be combined with molten anhydrous dextrose, this mass can then be introduced into an aqueous solution of cane sugar and the mixture can be heated to about 150° C. without vacuum to produce a product having a water content of more than 2.2%. This high water content has proven to be disadvantageous since the product agglomerates during a relatively long period of storage. This agglomeration has been prevented by addition of a desiccant (see Food Technologie, 1956, pp 57–60). In addition to the high expense of apparatus, the high drying temperature is also disadvantageous since partial decomposition of the constituents of the fruit juice, and especially of the aroma substances, occurs at this temperature.

It is also known that a lemon juice-sugar solution having a dry solids content of 60 to 66% can be vacuum dried. The product obtained in this way also possesses a high moisture content and is very highly hygroscopic, so that it too has to be packed with a desiccant (see Food Technologie, 1955, p 503). The method of freeze-drying a fruit juice-sugar mixture, which is also known, is very expensive in respect of apparatus and gives a very voluminous end product which, in addition, is still highly hygroscopic.

A process for the preparation of fruit juice-sugar granules in which the sugar is moistened with a fruit juice concentrate, the mass is dried by passing heated air over it and the dried material is then ground to granules, is described in DAS No. 1,299,994. A disadvantage of this process is the danger that the sugar crystals will largely dissolve and then, upon drying, will harden to give a hard, sparingly soluble mass. Moreover, it is not possible with this process to increase the content of fruit juice concentrate above 20%. The granules obtained in this way contain a maximum of only 6% of orange juice dry solids, a disadvantage for the desired fruity taste of the end product.

The object of the present invention is to prepare, without high apparatus expenditure and in a simple manner, fruit juice-sugar granules which are substantially anhydrous and capable of storage, which have a high content of fruit juice dry solids and which can be used as flavor improving agents in comestible products.

A first embodiment of the invention provides a process for the preparation of granules of fruit juice solids and sugar wherein the granules contain from about 8 to about 12% fruit juice solids with the balance being predominantly sugar and no more than 0.05% water which comprises spraying powdered sugar with a fruit juice in a fluidized bed granulator, granulating and drying the mixture at air temperatures no higher than 90° C., sieving the dried granules to a maximum grain size of 1 mm and redrying the sieved granules until the water content is no more than 0.05%.

In a further embodiment of the invention the fruit juice contains a sweetener and a dyestuff.

In a further embodiment, the fruit juice is fortified with the corresponding fruit juice concentrate to provide the requisite fruit juice solids.

In a further embodiment, the fruit juice is that of a citrus fruit.

In a further embodiment, the fruit juice is orange juice.

In a further embodiment, predominantly powdered sugar containing a minor amount of orange aroma powder is sprayed with orange juice containing minor amounts of saccharin and dyestuff in a fluidized bed granulator, the mixture is granulated and dried at air temperatures no higher than 90° C. for 15 to 30 minutes, and the dried granules are sieved to a maximum sieve size of 1 mm and redried until the water content is no more than 0.05%.

A further embodiment pertains to granules having a maximum grain size of 1 mm and comprising from about 8 to about 12% fruit juice solids with the balance being predominantly sugar and no more than 0.05% water.

A further embodiment pertains to comestible products comprising these granules, particularly but not exclusively, pharmaceutical compositions containing hydrolytically unstable pharmaceutical agents.

These and other objects are achieved, according to the invention, when fine-grained sugar is sprayed with fruit juice or fruit juice concentrate, such as orange juice, optionally together with additives such as pulverulent aroma substance, saccharin and dyestuffs, in a fluidized bed granulator, the temperature of the incoming air being at most 90° C., and after 15 to 30 minutes the resulting granules are sieved to a maximum grain size of 1 mm and are then dried for a further 30 minutes until the water content is at most 0.05%.

The granules obtained in this way can be mixed, either as such or after mixing in further additives, such as vitamin C, sodium citrate, anhydrous citric acid, sodium carbonate and sodium bicarbonate or other auxiliaries, with the pharmaceutical active compound which is sensitive to hydrolysis. The mixture obtained in this way is a powder which can be stored, is stable to hydrolysis and has a pleasant taste.

Preferably, the further additives, such as vitamin C, sodium citrate and citric acid, are first granulated separately before being combined with the granules.

The fruit juice-sugar granules obtained according to the invention cause substantially less hydrolysis than commercially available granules, when combined with hydrolytically unstable materials such as acetylsalicylic acid. Under normal conditions of storage, e.g. temperatures between 20 and 35° C., approximately seven times more free salicylic acid is formed when acetylsalicylic acid is combined with commercially available orange granules or a commercially available orange lyophylisate than when it is combined with the orange granules prepared according to the invention. The corresponding results are summarized in the table which follows:

TABLE

Hydrolysis of acetylsalicyclic acid in airtight packaging

| | Sample A | | | Sample B | | | Sample according to the invention | | |
|---|---|---|---|---|---|---|---|---|---|
| Temperature | Initially | 6 months | 12 months | Initially | 6 months | 12 months | Initially | 6 months | 12 months |
| 20° C | | 1.6% | 3.5% | | 1.8% | 3.4% | | 0.4% | 0.5% |

TABLE-continued

Hydrolysis of acetylsalicyclic acid in airtight packaging

| Temperature | Sample A | | | Sample B | | | Sample according to the invention | | |
|---|---|---|---|---|---|---|---|---|---|
| | Initially | 6 months | 12 months | Initially | 6 months | 12 months | Initially | 6 months | 12 months |
| 22° C | } 0.4% | 1.5% | 4.0% | } 0.5% | 1.9% | 4.2% | }' 0.3% | 0.4% | 0.6% |
| 35° C | | 4.0% | 22.0% | | 3.0% | 18.4% | | 0.8% | 3.5% |

The foregoing percentage data are for free salicylic acid relative to the amount of acetylsalicyclic acid present.

Sample A contains 4.0% of acetylsalicylic acid, 66.0% of commercial orange granules and 2.4% of ascorbic acid, the balance being sodium carbonate, sodium bicarbonate and citric acid.

Sample B consists of 4.0% of acetylsalicylic acid, 10.0% of orange lyophylisate and 2.4% of ascorbic acid, the balance being sodium carbonate, sodium bicarbonate and citric acid.

The sample according to the invention consists of 4.0% of acetylsalicylic acid, 67.4% of orange granules and 2.4% of ascorbic acid, the balance being sodium carbonate, sodium bicarbonate and citric acid.

Sugar-orange granules which can be mixed in a simple manner with acetylsalicyclic acid without rapid hydrolysis of the acetylsalicyclic acid to free salicylic acid and acetic acid have not been previously described. Constituents previously used in combination with orange granules have been, rather, only stable active compounds, such as vitamins, calcium or other trace elements. The present process makes it possible for the first time to prepare orange granules which contain a high proportion of orange juice dry solids (up to 12%) and which surprisingly, can be mixed with hydrolytically unstable substances such as acetylsalicyclic acid without the latter undergoing rapid hydrolysis to free salicylic acid.

The examples which follow will serve to further illustrate the present invention.

EXAMPLE 1

A mixture of 194.159 kg of powdered sugar and 3.333 kg of orange aroma powder are introduced into a fluidized bed granulator and sprayed at a rate of about 0.8l/minute with a solution of 44.666 kg of orange juice, into which 0.667 kg of saccharin and 0.16 kg of a dyestuff have been previously added and mixed. At the same time, the powder mixture is fluidized with incoming air warmed to 80° C. Spraying is interrupted at intervals of about 2 minutes and the filters are shaken for about 15 seconds. After all of the solution has been sprayed in, the resulting granules are dried for 25 minutes and sieved to a maximum grain size of 1 mm and then dried for a further 30 minutes in the fluidized bed granulator with incoming air at a temperature of 90° C. The resulting granules show a water content of no more than 0.05%.

EXAMPLE 2

(Preparation of vitamin C granules)

Twenty-four kilograms of vitamin C, 120.6 g or sodium citrate, 29.0 g of anhydrous citric acid, 0.42 g of a dyestuff and 20 kg of methanol are kneaded in a planetary kneader. The mass is then pressed through a sieve with a mesh width of 2 mm and dried in a fluidized bed drying cabinet until the water content is no more than 0.05%.

EXAMPLE 3

(Preparation of a finished mixture containing acetylsalicylic acid)

Six hundred seventy-five kilograms of orange juice granules and 40 kg of acetylsalicyclic acid are mixed together with 173.5 kg of vitamin C granules (according to Example 2), 91.5 kg of sodium bicarbonate and 20 kg of sodium carbonate for 25 minutes. The finished powder, which under conditions encountered in practice remains readily pourable, is filled in 5 g portions in a known manner.

What is claimed is:

1. Process for the preparation of a pharmaceutical composition comprising granules of citrus fruit juice solids and sugar wherein the granules contain from about 8 to about 12% citrus fruit juice solids with the balance being predominantly sugar and no more than 0.05% water and a hydrolytically unstable pharmaceutical agent which comprises spraying fluidized powdered sugar in a fluidized bed granulator with an unconcentrated citrus fruit juice, granulating and drying the mixture at air temperatures no higher than 90° C., sieving the dried granules to a maximum grain size of 1 mm, redrying the sieved granules until the water content is no more than 0.05% and combining the sieved granules with a hydrolytically unstable pharmaceutical agent.

2. Process according to claim 1 wherein the citrus fruit juice contains a sweetener and a dyestuff.

3. Process according to claim 1 wherein the citrus fruit juice is fortified with the corresponding citrus fruit juice concentrate to provide the requisite fruit juice solids.

4. Process according to claim 1 wherein the fruit juice is orange juice.

5. Process according to claim 1 wherein predominantly powdered sugar containing a minor amount of orange aroma powder is sprayed with orange juice containing minor amounts of saccharin and dyestuff in a fluidized bed granulator, granulating and drying the mixture at air temperatures no higher than 90° C. for 15 to 30 minutes, sieving the dried granules to a maximum sieve size of 1 mm, redrying the sieved granules until the water content is no more than 0.05% and combining the sieved granules with acetylsalicyclic acid.

6. Process according to claim 5 wherein the orange juice is fortified with orange juice concentrate to provide the requisite orange juice solids.

7. A pharmaceutical composition comprising a hydrolytically unstable pharmaceutical agent in combination with granules having a maximum grain size of 1 mm and comprising from about 8 to 12% citrus fruit juice solids with the balance of said granules being predominantly sugar and no more than 0.05% water.

8. A pharmaceutical composition according to claim 7 wherein the citrus fruit juice solids are those of orange juice.

9. A pharmaceutical composition according to claim 7 wherein the hydrolytically unstable pharmaceutical agent is acetylsalicyclic acid.

10. A pharmaceutical composition according to claim 7 wherein said granules further contain vitamin C.

* * * * *